Figure 1:
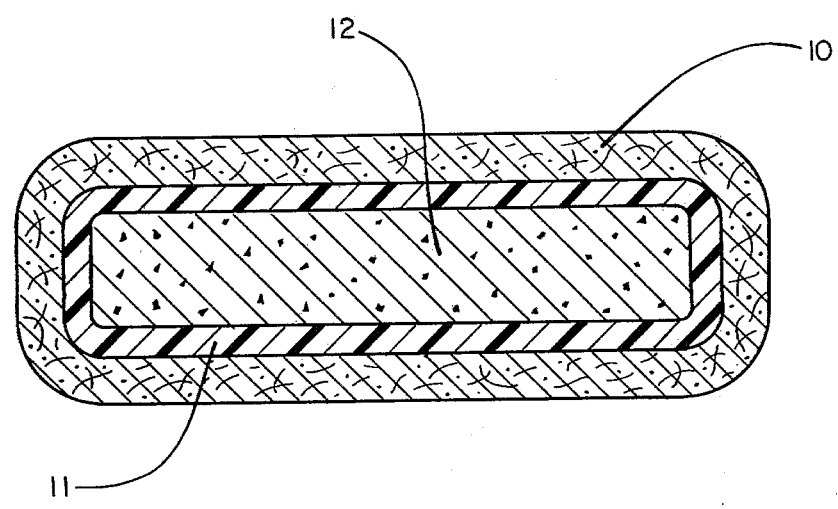

United States Patent [19]

Jackson

[11] 4,335,722

[45] Jun. 22, 1982

[54] WRAPPED SUPERABSORBENT CORE TAMPON

[75] Inventor: David M. Jackson, Appleton, Wis.

[73] Assignee: Kimberly-Clark Corporation, Neenah, Wis.

[21] Appl. No.: 235,100

[22] Filed: Feb. 17, 1981

[51] Int. Cl.³ .............................................. A61F 13/20
[52] U.S. Cl. .................................................. 128/285
[58] Field of Search .................... 128/285, 290 R, 287, 128/296

[56] References Cited

U.S. PATENT DOCUMENTS

| | | | |
|---|---|---|---|
| 3,073,309 | 1/1963 | Mosier | 128/290 R |
| 3,078,849 | 2/1963 | Morse | 128/290 R |
| 3,371,666 | 3/1968 | Lewing | 128/285 |
| 4,055,180 | 10/1977 | Karami | 128/296 |

*Primary Examiner*—C. Fred Rosenbaum
*Attorney, Agent, or Firm*—Howard Olevsky; William D. Herrick

[57] ABSTRACT

A tampon having an absorbent matrix with a superabsorbent material as a core is provided. The superabsorbent material is at least partially surrounded by a water dispersible coating and both the core and coating are surrounded by nonsuperabsorbent absorbents.

5 Claims, 1 Drawing Figure

WRAPPED SUPERABSORBENT CORE TAMPON

BACKGROUND OF THE INVENTION

Superabsorbent materials have found particular utility in tampons because of their ability to rapidly absorb large volumes of material in a relatively short time. Due to the relatively small size of a tampon compared to a sanitary napkin, absorption per unit volume can be a critical feature in measuring the performance of the tampon. For purposes of this invention a superabsorbent is defined as a material which may be either fibrous or nonfibrous in form but which develops capillary suction pressure of at least 25 centimeters of water when a gram of such material has absorbed 5 milliliters of physiological saline solution.

It is well known, however, that there are problems associated with the presence of superabsorbent material in tampons. Particularly acute is the difficulty associated with withdrawal of tampons containing superabsorbent material. Due to the rapid uptake of fluid by superabsorbent material a negative or suction pressure is built up on the surface. If this material is allowed to contact the walls of the vagina or be in close proximity thereto, withdrawal entails a physical force needed to separate the suction forces exerted on the walls of the vagina from the source of the pressure i.e. the superabsorbent.

There have been several attempts in the past to provide means for utilizing the superabsorbent capacity while minimizing the affect of the superabsorbent derived capillary suction. South African Patent No. 77/3309, for example, discloses a tampon in which a superabsorbent is wrapped in tissue and a nonwoven wrap. U.S. Pat. No. 4,056,103 discloses utilizing a wrap which will retain some measure of fluid to act as a lubricant. Attempts have been made to apply emollient coatings which are fluid and water soluble to a wrapped tampon to minimize the effect of the negative suction pressure. Additionally, it is known to utilize a mixture of superabsorbent and conventional cellulosic absorbents in an attempt to minimize the suction pressure associated with superabsorbents.

It is also known to utilize water soluble film in conjunction with a tampon. U.S. Pat. No. 3,371,666 discloses a tampon having a multiplicity of layers of two different types. One of the types of layers alternating with conventional absorbents is a thin water soluble film such as carboxymethylcellulose which itself acts as an absorbent component.

SUMMARY OF THE INVENTION

According to this invention a tampon having a superabsorbent core is provided with a covering of a water dispersible film. The film and the superabsorbent core is surrounded by nonsuperabsorbent material such as for example, rayon. By structuring the tampon in this manner, the superabsorbent material does not act until the outer layer of absorbent material has become almost completely saturated and the water dispersible film has been dissolved. In this manner, both the location of the superabsorbent material control to the absorbent matrix itself and its restriction of availability until saturation is accomplished tend to minimize the suction pressure traditionally associated with the use of these materials. In other words, the superabsorbent material is only utilized as an absorbent after the outer layer is saturated and there is a sufficient fluid barrier between the vaginal walls and the superabsorbent material surface to minimize the negative pressure which might otherwise occur. The utilization of a separate barrier layer acts to insure that the superabsorbent material only is used as an absorbent when the absorptive capacity of the outer absorbent layer has been exhausted. The invention can be more easily understood by reference to the drawing in which FIG. 1 is an enlarged representational view of a cross section of a noncompressed pledget of a tampon according to this invention in which the superabsorbent material 12 which can be either in fiber or powder form or sheet form or combination thereof as shown completely surrounded by a water dispersible film forming layer 11. Completely encircling these two components is conventional absorbent material 10 e.g. cellulosic fibers, polyester or polyolefin fibers (which may require surfactant treatment) or combinations thereof which is preferably rayon fibers of staple length.

While the absorbent component here is shown without an outer wrap, such a wrap of the type disclosed in the prior art may be added if desired to minimize sloughing or even further enhance the ease of withdrawal although the use of such a wrap for enhancing withdrawal ease is not necessary according to the teachings of this invention.

A particularly preferred superabsorbent material is known as sheet-10 and is made by National Starch. This material is a continuous and uniform laminate consisting of two tissue layers around a starch-polyacrylate graft copolymer superabsorbent film core.

The film forming coating material is preferably readily water dispersible and also may act to immobilize aqueous fluid such as menses in and of itself by increasing the viscosity thereof as it dissolves. Materials suitable for formation of films according to this invention are gelation, starches, hydroxyalkyl celluloses and particularly preferred is polyvinyl alcohol. The coating should be thick enough to cover at least a portion of the pledget. It should also be thin enough to disperse rapidly upon fluid contact i.e. generally on the order of 0.5 mil depending on the film former. While FIG. 1 shows the coating around the entire surface of the superabsorbent material, such a complete surface coating may not be necessary to bring about satisfactory results. Even the selective coating of certain surfaces will enhance the release capabilities of the tampon of this invention.

It is currently preferred that the relative weights of the absorbent components be such that the superabsorbent component is present between about 10 and 50% by weight of the entire pledget. The variance in weights between the components is dependent upon the amount of absorbency desired to be built into the tampon.

Tampons according to this invention can be treated as conventional tampons containing cellulosic material and, indeed, it is presently preferred that the tampon pledget after forming be subjected to compression and/or heat setting to prepare for subsequent insertion which can be either digitally or by mechanical insertion aids such as a tube type telescoping inserter. A withdrawal string is affixed at the base of the tampon in any manner well known in the art.

What is claimed is:
1. A tampon having an absorbent matrix comprising:
(a) a superabsorbent core material;
(b) A nontoxic water soluble coating material at least partially covering said superabsorbent core; and

(c) an outer absorbent layer surrounding said superabsorbent and said coating.

2. The tampon according to claim 1 wherein the coating material is a film forming polymer.

3. The tampon according to claim 2 wherein the coating material is polyvinyl alcohol.

4. The tampon according to claim 1 wherein the superabsorbent is between about 10 and 50% by weight of the absorbent matrix.

5. The tampon according to claim 1 wherein the coating increases the viscosity of the aqueous media as it dissolves therein.

* * * * *